(12) United States Patent
Levene et al.

(10) Patent No.: US 8,755,488 B2
(45) Date of Patent: Jun. 17, 2014

(54) VOLTAGE MODULATED X-RAY TUBE

(75) Inventors: Simha Levene, D. N. Hanegev (IL); Amiaz Altman, Tel Aviv (IL)

(73) Assignee: Koninklijke Philips N.V., Eindhoven (NL)

( * ) Notice: Subject to any disclaimer, the term of this patent is extended or adjusted under 35 U.S.C. 154(b) by 720 days.

(21) Appl. No.: 13/054,814

(22) PCT Filed: Jul. 22, 2009

(86) PCT No.: PCT/IB2009/053183
§ 371 (c)(1),
(2), (4) Date: Jan. 19, 2011

(87) PCT Pub. No.: WO2010/015960
PCT Pub. Date: Feb. 11, 2010

(65) Prior Publication Data
US 2011/0122996 A1    May 26, 2011

Related U.S. Application Data

(60) Provisional application No. 61/087,193, filed on Aug. 8, 2008.

(51) Int. Cl.
G01N 23/04 (2006.01)
H05G 1/32 (2006.01)

(52) U.S. Cl.
USPC ............................................ 378/62; 378/111

(58) Field of Classification Search
USPC ............................ 378/16, 62, 108–112, 145
See application file for complete search history.

(56) References Cited

U.S. PATENT DOCUMENTS

| 5,661,774 A | 8/1997 | Gordon et al. |
| 6,215,850 B1 | 4/2001 | Blake et al. |
| 6,553,096 B1 | 4/2003 | Zhou et al. |
| 6,816,573 B2 | 11/2004 | Hirano et al. |
| 7,151,818 B1 | 12/2006 | Hanington et al. |
| 7,209,537 B2 | 4/2007 | Popescu |
| 2004/0101087 A1 | 5/2004 | Hsieh et al. |
| 2005/0078794 A1 | 4/2005 | Leek |

FOREIGN PATENT DOCUMENTS

| CN | 1173637 A | 2/1998 |
| CN | 101101848 A | 1/2008 |
| DE | 102004051820 A1 | 5/2006 |
| EP | 1355321 A2 | 10/2003 |
| WO | 2005009206 A2 | 2/2005 |
| WO | 2006114716 A2 | 11/2006 |
| WO | 2007017773 A2 | 2/2007 |

OTHER PUBLICATIONS

Zhang, J., et al.; Multiplexing Radiography for Ultra-Fast Computed Tomography; 2007; AAPM Meeting, Minneapolis, MN; 3 pages.

*Primary Examiner* — Irakli Kiknadze

(57) ABSTRACT

A system comprises a radiation source (110), including a anode (112) and a cathode (114), a high voltage generator (202) that generates a source voltage that is applied across the anode (112) and cathode (114), wherein the source voltage accelerates electrons from the cathode (114) towards the anode (112), and a modulation wave generator (204) that generates a modulation voltage wave having a non-zero amplitude, which is combined with and modulates the source voltage between at least two different voltages.

26 Claims, 3 Drawing Sheets

VOLTAGE MODULATED X-RAY TUBE

CROSS REFERENCE TO RELATED APPLICATIONS

This application claims the benefit of U.S. provisional application Ser. No. 61/087,193 filed Aug. 8, 2008, which is incorporated herein by reference.

The following generally relates to x-ray tubes, and finds particular application to computed tomography (CT). However, it also amenable to other medical imaging applications and to non-medical imaging applications, including baggage handling.

A conventional computed tomography (CT) scanner includes an x-ray tube mounted on a rotatable gantry opposite a detector array. The x-ray tube rotates around an examination region located between the x-ray tube and the detector array and emits radiation that traverses the examination region and a subject and/or object disposed therein. The detector array detects radiation that traverses the examination region and generates a signal indicative of the examination region. A reconstructor reconstructs the signal to generate volumetric image data, which can be used to generate one or more images of the scanned subject and/or object. The resulting image generally includes pixels that typically are represented in terms of gray scale values corresponding to relative radiodensity. Such information reflects the attenuation characteristics of the scanned subject and/or object, and generally shows structure such as anatomical structures within a patient, physical structures within an inanimate object, and the like.

The detected radiation also includes spectral information as the absorption of the radiation by the subject and/or object is dependent on the energy of the photons traversing therethrough. Such x-ray spectral information provides additional information such as information indicative of the atomic, elemental or material composition of tissue and/or the object. However, with conventional CT the projection data does not reflect the spectral characteristics as the signal output by the one or more detectors as proportional to the energy fluence integrated over the whole energy spectrum. In spectral CT, the spectral characteristics are leveraged to provide further information such as atomic or elemental composition information. One approach for obtaining spectral information is to use a detector that includes at least two photosensors with different spectral sensitivities. Another approach for obtaining spectral information is to switch the emission voltage of a single x-ray tube between two different effective voltages and detect radiation and generate separate images for each emission voltage. Unfortunately, conventional emission spectrum switching techniques have limited switching speed. Another approach for obtaining spectral information is to utilize two x-ray tubes, operated at different anode voltages, and operate the tubes alternately for successive scans or successive views. However, this technique tends to be very cumbersome and includes expensive instruments. Thus, there is an unresolved need for other and/or improved techniques.

Aspects of the present application address the above-referenced matters and others.

According to one aspect, a system comprises a radiation source, including an anode and a cathode, a high voltage generator that generates a source voltage that is applied across the anode and cathode, wherein the source voltage accelerates electrons from the cathode towards the anode, and a modulation wave generator that generates a modulation voltage wave having a non-zero amplitude, which is combined with and modulates the source voltage between at least two different voltages.

According to another aspect, a method includes generating a high voltage for a radiation source of an imaging system, wherein the high voltage is applied across an anode and cathode of the radiation source and the radiation source generates radiation based on the high voltage, generating a modulation voltage wave, and modulating the high voltage with the modulation voltage wave between at least two different voltages.

According to another aspect, an imaging system includes a radiation source that rotates about an examination region and emits radiation that traverses the examination region, wherein the radiation source generates radiation having an energy spectrum that is selectively alternately modulated between at least two different energy spectrums during an imaging procedure. The imaging system further includes a modulation wave generator that generates a modulation voltage wave that modulates the energy spectrum between the at least two different energy spectrums during the imaging procedure. The imaging system further includes a radiation sensitive detector that detects radiation traversing the examination region and generates a signal indicative thereof.

The invention may take form in various components and arrangements of components, and in various steps and arrangements of steps. The drawings are only for purposes of illustrating the preferred embodiments and are not to be construed as limiting the invention.

Figure 1:
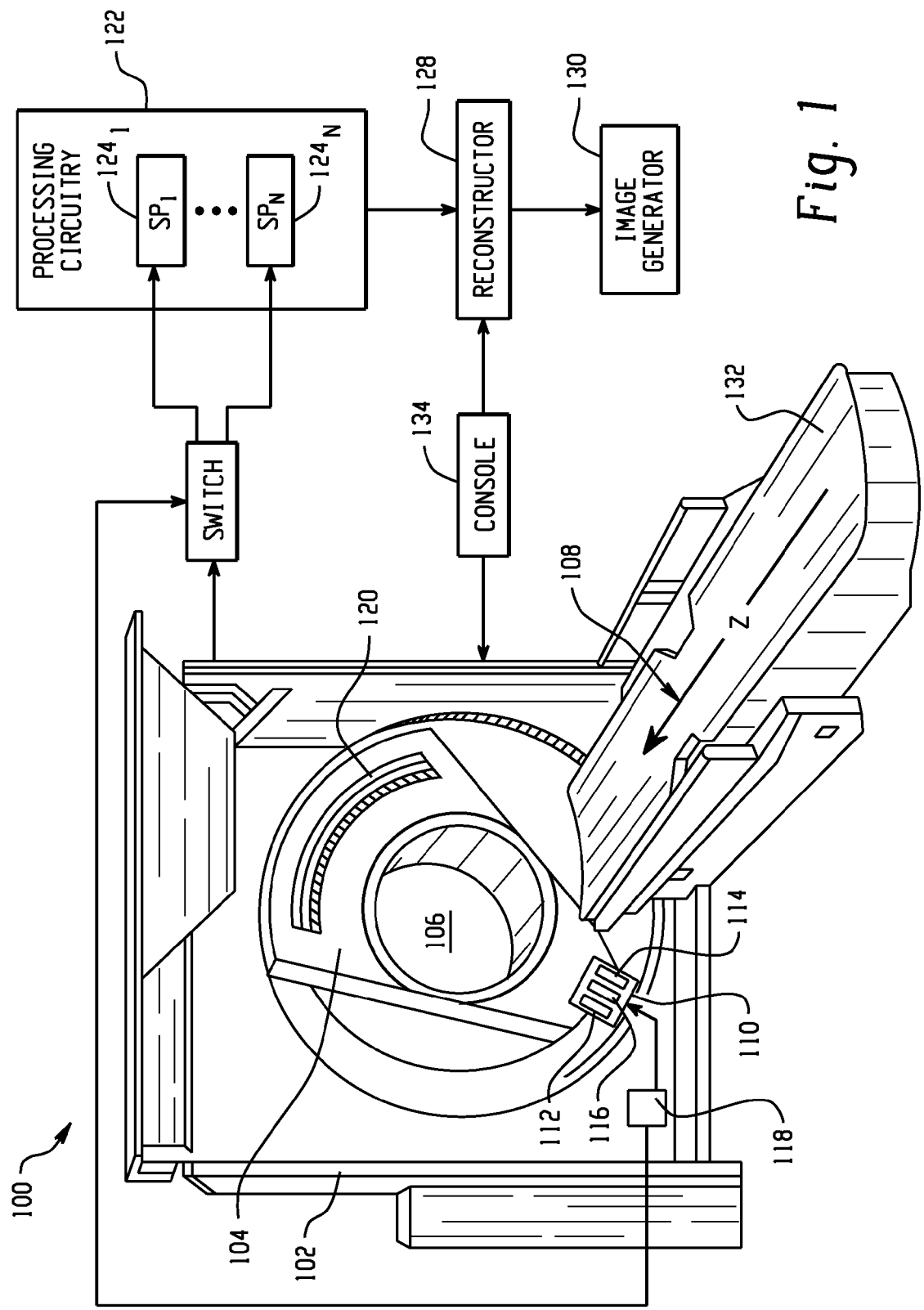
FIG. 1 illustrates an example imaging system.

FIG. 1 illustrates a computed tomography (CT) scanner 100 that includes a stationary gantry 102 and a rotating gantry 104, which is rotatably supported by the stationary gantry 102. The rotating gantry 104 rotates around an examination region 106 about a longitudinal or z-axis 108.

A radiation source 110 is supported by and rotates with the rotating gantry 104 around the examination region 106. The radiation source 110 emits radiation, which is collimated by a collimator to produce a generally fan, wedge, or cone shaped radiation beam that traverses the examination region 106. In the illustrated example (See also FIG. 2), the radiation source 110 is an x-ray tube such as an electrostatically-focused triode, including an anode 112, a cathode 114 and a beam switching grid 116. In other embodiments, the radiation source 110 may include one or more other grids (tetrode, pentode, etc.). In addition, the radiation source 110 may alternatively be magnetically or otherwise focused.

A radiation source control system 118 controls the voltages supplied to the radiation source 110. Such control includes modulating the source voltage between at least two different voltages, or emission spectrums. As described in greater detail below, in one instance the source voltage is modulated as such by modulating a non-zero reference high voltage with a modulation wave having an amplitude that combines with the reference voltage to switch between the at least two different voltages. The radiation source control system 118 also triggers modulation of the grid voltage to turn the x-ray beam on and off and a focusing electrode voltage to focus the electron beam in synchronization with the modulating of the reference voltage.

A radiation sensitive detector 120 detects photons that traverse the examination region 106 and generates a signal indicative thereof. Suitable detectors include direct conversion detectors or a scintillator-based detector that includes a scintillator in optical communication with a photodiode. In another embodiment, the detector 120 includes an energy-resolving detector such as the energy-resolving detector described in connection with patent application number PCT/

IB2006/051091, publication number WO2006114716 A3, filed Apr. 10, 2006, and entitled "DOUBLE DECKER DETECTOR FOR SPECTRAL CT."

Such an energy-resolving detector may include a first region with a first spectral sensitivity and at least a second region with a second different spectral sensitivity, wherein the first region detects photons having energy corresponding to the first spectral sensitivity and generates signals indicative thereof, and the second region detects photons having energy corresponding to the second spectral sensitivity and generates signals indicative thereof. Using such detectors may provide additional spectral information that can improve spectral resolution.

Processing circuitry 122 processes the signal. The illustrated processing circuitry 122 includes multiple sub-processor $124_1, \ldots, 124_N$, wherein N is an integer greater than one. Each of the sub-processors 124 is configured to process signals for different emission spectrums. For example, in the illustrated embodiment the sub-processor $124_1$ ($SP_1$) is configured to process signals for a first emission spectrum, and the sub-processor $124_N$ ($SP_N$) is configured to process signals for an Nth emission spectrum.

A switch 126 routes the signal to the appropriate sub-processor 124. As described in greater detail below, the switch 126 switches in coordination with the modulation of the radiation source voltage.

A reconstructor 128 reconstructs the processed signals based on the emission spectrums and respectively generates volumetric image data indicative of the composition of the object or person scanned.

An image generator 130 generates an image based on the volumetric image data. In one instance, this includes generating a first image for a first source emission spectrum and a second image for a second source emission spectrum. A comparison of such images provides spectral information, which may be used to differentiate between the atomic or elemental compositions of tissue and/or inanimate objects.

A support 132, such as a couch, supports an object or subject such as a patient for a scan.

A general purpose computing system serves as an operator console 134. Software resident on the console 134 allows the operator to control the operation of the system 100. Such control may include selecting a scan protocol such as a spectral imaging protocol that modulates the source voltage to switch emission spectrums.

It is to be appreciated that by rapidly switching the source voltage via the modulation wave at view (integration interval) frequency or more, or at a frequency corresponding to rows of detectors or a two dimensional matrix of detectors, relative motion between images generated with different spectral sensitivities can be reduced. In one instance, this may improve spectral resolution relative to a configuration that does not modulate the source voltage. This may also improve spectral resolution relative to a system that switches voltages but not with sharply square waves, but with voltages that slide gently up and down.

Figure 2:
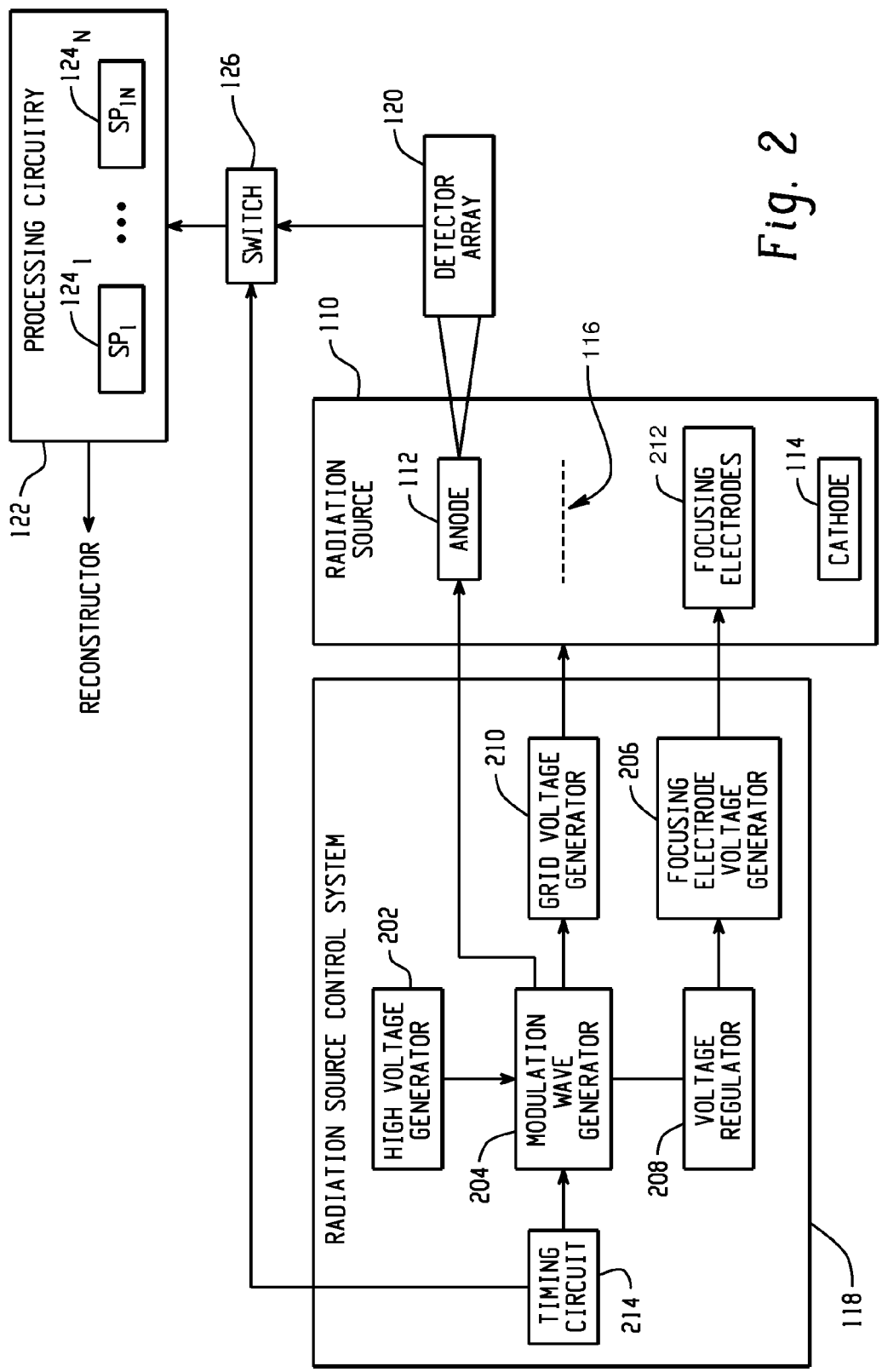
FIG. 2 illustrates an example radiation source controller.

FIG. 2 illustrates a non-limiting example of the radiation source control system 118. The illustrated radiation source control system 118 includes a high voltage generator 202 that generates high voltage for the radiation source 110. Such a voltage can be in a range of 50 kV to 150 kV such as 110 kV or other voltage. The voltage generated for a particular scan may depend on the different voltages defined in a selected spectral protocol, for example, a protocol tailored to the needs of the diagnosis and the size of the patient.

A modulation wave generator 204 generates a modulation wave for modulating the generated high voltage. In this example, the modulation wave generator 204 generates a generally square wave modulation voltage, which modulates the high voltage between two different voltages. For example, a 100 kV square modulation wave with an amplitude of about ±50 kV would modulate a 100 kV high voltage signal from about 50 kV to about 150 kV. In another example, a 60 kV square modulation wave with an amplitude of 30 kV (±30 kV) would modulate a 110 kV high voltage signal from about 80 kV to about 140 kV. The value of the wave may depend on the voltages defined in the selected spectral protocol and the value of the generated high voltage. In another embodiment, the modulation wave may be differently shaped. It is also to be appreciated that the voltage can be modulated in N steps, such as 80 kV, 90 kV, 100 kV . . . 140 kV. In such an instance, generally, the jumps between the steps should be as sharp as possible. Sharps jumps may mitigate reduction of spectral contrast by generation of x-rays at intermediate anode voltages, which may occur with an electromagnetic tube.

The modulated high voltage is applied across the anode 112 and the cathode 114 and accelerates electrons from the cathode 114 to the anode 112. Such electrons may be "boiled" off a filament of the anode 112, for example, via thermionic emission or otherwise provided. The electron flow provides a current flow from the cathode 114 to the anode 112, and the electrons strike the anode 112, generating x-radiation and heat.

Focusing electrodes 212 focus the accelerated electrons at a target region on the anode 112. A focusing electrode voltage generator 206 provides a focusing electrode voltage. Generally, the focusing electrode voltage depends on the voltage applied across the anode 112 and the cathode 114, a selected resolution, and/or other characteristic. Focus is maintained during source voltage modulation by applying a fraction of the modulation wave amplitude to the focusing electrodes 212. In the illustrated embodiment, a voltage regulator 208 scales the amplitude accordingly.

The focusing electrode voltage modulates in coordination or synchronization with the modulation of the high voltage. Generally, modulation of the focusing electrode voltage is proportional to the modulation of the high voltage. By way of non-limiting example, in one instance, the focusing electrode voltage is modulated between −2 kV and −4 kV in coordination with modulating the high voltage between 75 kV and 150 kV. A suitable focusing electrode voltage focuses the electrons so as to produce a relatively narrow and short focal spot, which may mitigate blurring, which can occur with a larger focal spot.

A grid voltage generator 210 generates a grid voltage for a switching grid 116, which allows or inhibits current or electrons to flow from the cathode 114 to the anode 112. In one instance, the grid voltage generator 210 modulates the grid voltage in coordination or synchronization with the modulation of the high voltage. This may mitigate "bunching" of the electrons at the cathode 114 at lower anode voltages. This may also draw higher currents from the anode 112 at lower anode voltages where x-ray fluence is relatively low. As such, a same current level may be maintained regardless of the amplitude of the modulated high voltage. In one embodiment, the grid voltage modulation may be used to increase anode current and tube output at lower anode voltages, to compensate for the reduced effectiveness of the lower energy x-rays generated. In one embodiment, the grid voltage generator 208 is omitted.

A timing circuit 214 generates a signal which triggers the modulation wave generator 204. In one instance, the timing circuit 214 triggers the modulation wave generator 204 to modulate the high voltages at a frequency of about view frequency (the integration interval frequency), or at a frequency corresponding to rows of detectors or complete detector tiles, which include a two dimensional matrix of photosensors. Generally, the view frequency is the frequency at which data is captured, or the integration interval frequency. By way of non-limiting example, the timing circuit 214 may trigger the modulation wave generator 204 at a frequency between 10 and 50 kHz such as 30 kHz. The timing circuit 214 signal also triggers the switch 126 to switch to an appropriate sub-processor in coordination or synchronization with the modulation of the high voltage, or it may simply trigger software that stores data generated from a single processor to an appropriate memory location.

By way of example, in one instance the signal may trigger the wave generator 204 to generate +30 kV, which combines with 110 kV supplied by the high voltage power supply, in order to apply 140 kV across the radiation source 110. In this instance, the signal also triggers the switch 126 so that the detector signal is processed by signal processor $SP_{140kV}$ and/or stored in corresponding memory. In another instance, the signal may trigger the wave generator 204 to generate −30 kV, which combines with 110 kV supplied by the high voltage power supply, in order to apply 80 kV across the radiation source 110. In this instance, the signal also triggers the switch 126 so that the detector signal is processed by signal processor $SP_{80kV}$ and/or is stored in corresponding memory.

As noted above, the processing circuitry 122 employs a particular sub-processor 124 based on the emission spectrum. The resulting energy-resolved signals are provided to the reconstructor 128, which, as described above, reconstructs the signals to generate volumetric image data. Also discussed above, the image generator 130 generates spectral images, based on the volumetric image data, which may be used to differentiate between the atomic or elemental compositions of scanned tissue and/or inanimate object.

It is to be appreciated that by rapidly switching the source voltage via the modulation wave at view frequency or a frequency corresponding to rows of detectors or a two dimensional matrix detectors, motion blur between images generated with different spectral sensitivities can be reduced. In one instance, this may improve spectral resolution relative to a configuration that does not modulate the source voltage. Further, by switching with very square waves, without intervening intermediate voltages, spectral resolution definition may be improved relative to a configuration using sinusoidal or triangular wave modulation, or modulation in which the square waves have rounded profiles.

Figure 3:
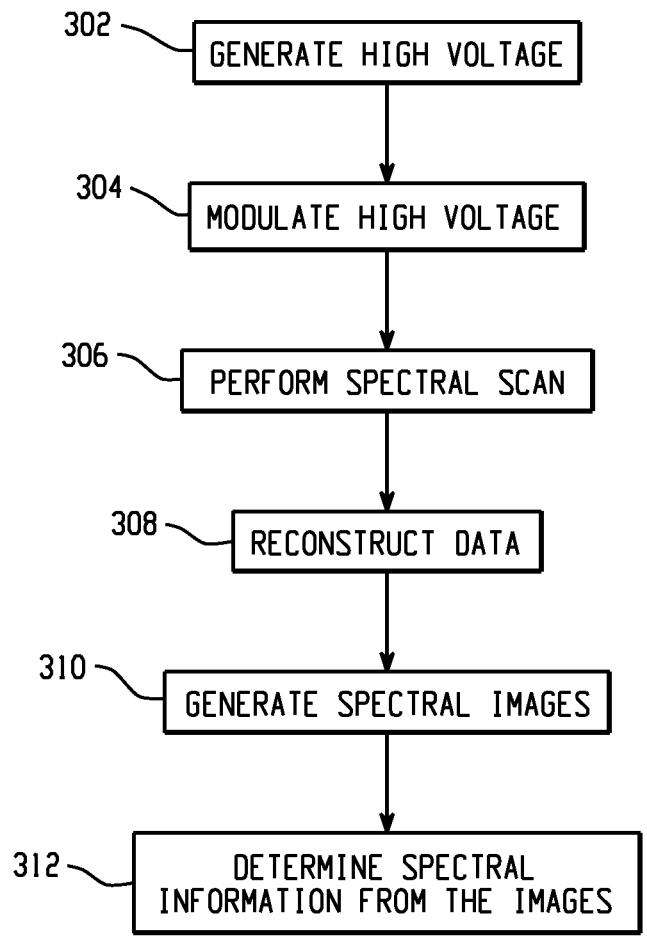
FIG. 3 illustrates an example method.

FIG. 3 illustrates a method. At 302, a high voltage is generated for the radiation source 110. At 304, the high voltage is modulated between at least two different voltages based on a modulation wave. As discussed herein, this may include generating a square or other shaped stepped wave having an amplitude to modulate the high voltage accordingly and at a frequency that may improve spectral resolution. At 306, a spectral scan is performed in which data is independently captured for each of the at least two different emission spectrums. At 308, the spectral data is reconstructed. At 310, spectral images are generated for the at least two of the different emission spectrums. At 312, the images are compared to determine atomic, elemental and composition differences.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

We claim:

1. A system, comprising:
a radiation source that generates radiation, the radiation source, including:
an anode; and
a cathode;
a high voltage generator that generates a source voltage that is applied across the anode and cathode, wherein the source voltage accelerates electrons from the cathode towards the anode; and
a modulation wave generator that generates a modulation voltage wave having a non-zero amplitude, which is combined with and modulates the source voltage between at least two different voltages.

2. The system of claim 1, wherein the modulation voltage wave is a square wave.

3. The system of claim 1, further comprising:
timing circuit that triggers the modulation wave generator to generate a modulation voltage wave that modulates the source voltage between the at least two different voltages at a frequency in a range between about 20 and 50.

4. The system of claim 1, wherein the cathode includes a filament, and the electrons accelerate from the filament to the anode.

5. The system of claim 1, wherein the radiation source further includes focusing electrodes that focus the accelerated electrons on a target region of the anode, and further including a focusing electrode voltage generator that generates a focusing electrode voltage that is applied across the focusing electrodes, wherein the focusing electrode voltage modulates in coordination with the modulation of the source voltage.

6. The system of claim 5, further including a voltage regulator that scales down the value of the modulation voltage wave and supplies the scaled down value to the focusing electrode voltage generator, which generates the focusing electrode voltage based on the scaled down value.

7. The system of claim 5, wherein the focusing electrode voltage and the source voltage are proportionally modulated.

8. The system of claim 1, wherein the radiation source further includes a switching grid, located between the anode and the cathode, which when turned on inhibits electron flow from the cathode to the anode.

9. The system of claim 8, further including a grid voltage generator that generates a grid voltage that selectively turns the switching grid on and off.

10. The system of claim 8, wherein the grid voltage and the source voltage are synchronously modulated, wherein the grid voltage increases at lower source voltages, thereby increasing an anode current at the lower source voltages where electrons having lesser energy per electron generate fewer x-rays.

11. The system of claim 1, further including a timing circuit that generates a signal that triggers the modulation wave generator to modulate the source voltage.

12. The system of claim 11, wherein the source voltage modulates each integration interval.

13. A method, comprising:
generating a high voltage for a radiation source of an imaging system, wherein the high voltage is applied across an anode and cathode of the radiation source and the radiation source generates radiation based on the high voltage;
generating a modulation voltage wave; and
modulating the high voltage with the modulation voltage wave between at least two different voltages.

14. The method system of claim 13, further including modulating a focusing electrode voltage applied across focusing electrodes of the radiation source in coordination with modulating the source voltage.

15. The method system of claim 13, further including modulating a grid voltage for a control grid of the radiation source in coordination with modulating the source voltage.

16. The method system of claim 13, further including:
   detecting the radiation generated by the radiation source;
   generating a signal indicative of the detected radiation; and
   routing the signal to signal processor based on a value of the modulated source voltage.

17. The method of claim 13, further including generating a first image based on data corresponding to a first source voltage and a second image based on data corresponding to a second source voltage, wherein the first and second images together provide atomic information about a scanned subject or object.

18. The method system of claim 13, further including a switch that routes the signal based the modulated source voltage, wherein the switch routes the signal to at least two different sub-processors based on the modulated source voltage.

19. The method system of claim 13, wherein the modulation voltage wave is a square wave.

20. An imaging system, comprising:
   a radiation source that rotates about an examination region and emits radiation that traverses the examination region, wherein the radiation source emits radiation having an energy spectrum that is selectively alternately modulated between at least two different energy spectrums during an imaging procedure;
   a modulation wave generator that generates a modulation voltage wave that modulates the energy spectrum between the at least two different energy spectrums during the imaging procedure; and
   a radiation sensitive detector array that detects radiation traversing the examination region and generates a signal indicative thereof.

21. The system of claim 20, further including an image generator that generates a first image based on the first energy-resolved output signal and a second image based on the second energy-resolved output signal.

22. The system of claim 20, further including comparing the first and second images to determine spectral information about a subject or object being imaged.

23. The system of claim 22, the radiation source, further including:
   a switching grid disposed between the anode and the cathode, wherein the switching grid allows and inhibits a current to flow between the anode and the cathode in coordination with the modulation of the energy spectrum.

24. The system of claim 20, the detector, including:
   a plurality of radiation detection regions, wherein at least a first of the regions is sensitive to a first energy spectrum and at least a second of the regions is sensitive to a second different energy spectrum, and the first and second regions respectively produce first and second energy-resolved output signals indicative of their respective spectral sensitivities.

25. The system of claim 20, the radiation source, further including:
   focusing electrodes that focus the accelerated electrons on a target region of the anode, wherein a focusing electrode voltage modulates in coordination with the modulation of the energy spectrum.

26. The system of claim 20, further including a timing circuit that generates a signal that triggers the modulation wave generator to generate the modulation voltage wave.

* * * * *